(12) United States Patent
Ferre et al.

(10) Patent No.: US 6,445,943 B1
(45) Date of Patent: *Sep. 3, 2002

(54) POSITION TRACKING AND IMAGING SYSTEM FOR USE IN MEDICAL APPLICATIONS

(75) Inventors: Maurice R. Ferre, Boston; Peter D. Jakab, Sharon; James S. Tieman, Watertown, all of MA (US)

(73) Assignee: Visualization Technology, Inc., Lawrence, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/211,365

(22) Filed: Dec. 14, 1998

Related U.S. Application Data

(63) Continuation of application No. 08/768,305, filed on Dec. 17, 1996, which is a continuation of application No. 08/306,818, filed on Sep. 15, 1994, now Pat. No. 5,829,444.

(51) Int. Cl.$^7$ ................................................. A61B 5/05
(52) U.S. Cl. ....................................... 600/424; 606/130
(58) Field of Search ................................ 600/407, 415, 600/417, 424; 606/130

(56) References Cited

U.S. PATENT DOCUMENTS

| | | |
|---|---|---|
| 3,109,588 A | 11/1963 | Polhemus |
| 3,614,950 A | 10/1971 | Rabey |
| 3,644,825 A | 2/1972 | Davis, Jr. et al. |
| 3,821,469 A | 6/1974 | Whetstone et al. |
| 3,868,565 A | 2/1975 | Kuipers |
| 3,983,474 A | 9/1976 | Kuipers |
| 4,017,858 A | 4/1977 | Kuipers |
| 4,054,881 A | 10/1977 | Raab |

(List continued on next page.)

FOREIGN PATENT DOCUMENTS

| | | |
|---|---|---|
| DE | 482 439 | 1/1970 |
| DE | 4213426 | 1/1970 |
| DE | 3508730 | 9/1986 |

(List continued on next page.)

OTHER PUBLICATIONS

"Science Accessories Corporation—3–Dimensional sonic digitizer—Model GP–8–3D" (Aug. 1989) 2 pages.

A Frameless, Armless Navigational System for Computer Assisted Neurosurgy (May, 1991) by Kato, et al.

(List continued on next page.)

Primary Examiner—Brian L. Casler
(74) Attorney, Agent, or Firm—Fish & Richardson P.C.

(57) ABSTRACT

A system is disclosed for monitoring the position of a medical instrument with respect to a patient's body and for displaying at least one of a plurality of prerecorded images of said body responsive to the position of said medical instrument. In one embodiment the system includes a reference unit secured from movement with respect to the patient's body such that said reference unit is substantially immobile with respect to a target operation site. The system also includes a remote unit for attachment to the medical instrument. A field generator may be associated with one of the units for generating a position characteristic field in an area including the target operation site. One or more field sensors may be associated with either of the units responsive to the presence of the position characteristic field for producing one or more sensor output signals representative of said sensed field. A position detector in communication with the sensor output signal produces position data representative of the position of the remote unit with respect to the reference unit. An output display in communication with the position detector displays at least one of the prerecorded images responsive to the position data.

50 Claims, 5 Drawing Sheets

U.S. PATENT DOCUMENTS

| | | |
|---|---|---|
| 4,182,312 A | 1/1980 | Mushabac |
| 4,228,799 A | 10/1980 | Anichkov et al. |
| 4,256,112 A | 3/1981 | Kopf et al. |
| 4,262,306 A | 4/1981 | Renner |
| 4,298,874 A | 11/1981 | Kuipers |
| 4,314,251 A | 2/1982 | Raab |
| 4,319,136 A | 3/1982 | Jinkins |
| 4,328,548 A | 5/1982 | Crow et al. |
| 4,341,220 A | 7/1982 | Perry |
| 4,346,384 A | 8/1982 | Raab |
| 4,506,676 A | 3/1985 | Duska |
| 4,583,538 A | 4/1986 | Onik et al. |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,638,798 A | 1/1987 | Shelden et al. |
| 4,642,786 A | 2/1987 | Hansen |
| 4,651,732 A | 3/1987 | Frederick |
| 4,659,971 A | 4/1987 | Suzuki et al. |
| 4,660,970 A | 4/1987 | Ferrano |
| 4,688,037 A | 8/1987 | Krieg |
| 4,701,049 A | 10/1987 | Beckmann et al. |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,722,056 A | 1/1988 | Roberts et al. |
| 4,723,544 A | 2/1988 | Moore et al. |
| 4,733,969 A | 3/1988 | Case et al. |
| 4,737,032 A | 4/1988 | Addleman et al. |
| 4,737,794 A | 4/1988 | Jones |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,794,262 A | 12/1988 | Sato et al. |
| 4,804,261 A | 2/1989 | Kirschen |
| 4,805,615 A | 2/1989 | Carol et al. |
| 4,809,694 A | 3/1989 | Ferrara |
| 4,821,200 A | 4/1989 | Oberg |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,860,331 A | 8/1989 | Williams et al. |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,955,891 A | 9/1990 | Carol |
| 4,961,422 A | 10/1990 | Marchosky et al. |
| 4,991,579 A | 2/1991 | Allen |
| 5,016,639 A | 5/1991 | Allen |
| 5,017,139 A | 5/1991 | Mushabac |
| 5,027,818 A | 7/1991 | Bova et al. |
| 5,042,486 A | 8/1991 | Pfeiler et al. |
| 5,050,608 A | 9/1991 | Watanabe et al. |
| 5,078,140 A | 1/1992 | Kwoh |
| 5,086,401 A | 2/1992 | Glassman et al. |
| 5,094,241 A | 3/1992 | Allen |
| 5,097,839 A | 3/1992 | Allen |
| 5,098,426 A | 3/1992 | Sklar et al. |
| 5,099,846 A | 3/1992 | Hardy |
| 5,107,839 A | 4/1992 | Houdek et al. |
| 5,119,817 A | 6/1992 | Allen |
| 5,142,930 A | 9/1992 | Allen et al. |
| 5,143,076 A | 9/1992 | Hardy et al. |
| 5,178,164 A | 1/1993 | Allen |
| 5,186,174 A | 2/1993 | Schlondorff et al. |
| 5,193,106 A | 3/1993 | DeSena |
| 5,197,476 A | 3/1993 | Nowacki et al. |
| 5,207,688 A | 5/1993 | Carol |
| 5,211,164 A | 5/1993 | Allen |
| 5,211,165 A | 5/1993 | Dumoulin et al. |
| 5,224,049 A | 6/1993 | Mushabac |
| 5,230,338 A | 7/1993 | Allen et al. |
| 5,230,623 A | 7/1993 | Guthrie et al. |
| 5,251,127 A | 10/1993 | Raab |
| 5,257,998 A | 11/1993 | Ota et al. |
| 5,261,404 A | 11/1993 | Mick et al. |
| 5,279,309 A | 1/1994 | Taylor et al. |
| 5,285,787 A | 2/1994 | Machida |
| 5,299,253 A | 3/1994 | Wessels |
| 5,300,080 A | 4/1994 | Clayman et al. |
| 5,306,271 A | 4/1994 | Zinreich et al. |
| 5,307,072 A | 4/1994 | Jones, Jr. |
| 5,309,913 A | 5/1994 | Kormos et al. |
| 5,318,025 A | 6/1994 | Dumoulin et al. |
| 5,330,485 A | 7/1994 | Clayman et al. |
| 5,368,030 A | 11/1994 | Zinreich et al. |
| 5,383,454 A | 1/1995 | Bucholz |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,446,548 A | 8/1995 | Gerig et al. |
| 5,453,686 A | 9/1995 | Anderson |
| 5,457,641 A | 10/1995 | Zimmer et al. |
| 5,469,847 A | 11/1995 | Zinreich et al. |
| 5,480,439 A | 1/1996 | Bisek et al. |
| 5,483,961 A | 1/1996 | Kelly et al. |
| 5,514,146 A | 5/1996 | Lam et al. |
| 5,517,990 A | 5/1996 | Kalfas et al. |
| 5,551,429 A | 9/1996 | Fitzpatrick et al. |
| 5,558,091 A | 9/1996 | Acker et al. |
| 5,566,681 A | 10/1996 | Manwaring et al. |
| 5,568,384 A | 10/1996 | Robb et al. |
| 5,588,430 A | 12/1996 | Bora et al. |
| 5,600,330 A | 2/1997 | Blood |
| 5,615,132 A | 3/1997 | Horton et al. |
| 5,617,857 A | 4/1997 | Chader et al. |
| 5,622,170 A | 4/1997 | Schulz |
| 5,640,170 A | 6/1997 | Anderson |
| 5,646,524 A | 7/1997 | Gilboa |
| 5,676,673 A | 10/1997 | Ferre et al. |
| 5,695,500 A | 12/1997 | Taylor et al. |
| 5,718,241 A | 2/1998 | Ben-Haim et al. |
| 5,729,129 A | 3/1998 | Acker |
| 5,730,130 A | 3/1998 | Fitzpatrick et al. |
| 5,732,702 A | 3/1998 | Kalfas et al. |
| 5,738,096 A | 4/1998 | Ben-Haim |
| 5,752,513 A | 5/1998 | Acker et al. |

| | | | |
|---|---|---|---|
| 5,755,725 A | 5/1998 | Druais | |
| 5,769,861 A | 6/1998 | Vilsmeier | |
| 5,799,099 A | 8/1998 | Wang et al. | |
| 5,829,444 A | 11/1998 | Ferre et al. | |
| 5,868,675 A | 2/1999 | Henrion et al. | |
| 5,871,445 A | 2/1999 | Bucholz | |
| 5,891,034 A | 4/1999 | Bucholz | |
| 5,920,395 A | 7/1999 | Schulz | |
| 5,967,980 A | * 10/1999 | Ferre et al. | 600/424 |
| 5,971,997 A | 10/1999 | Guthrie et al. | |
| 6,076,008 A | 2/2000 | Bucholz | |
| 6,071,288 A | 6/2000 | Carol et al. | |
| 6,122,541 A | 9/2000 | Cosman et al. | |
| 6,165,181 A | 12/2000 | Heilbrun et al. | |

FOREIGN PATENT DOCUMENTS

| | | |
|---|---|---|
| EP | 62941 | 10/1982 |
| EP | 0600610 A | 6/1994 |
| FR | 2618211 | 1/1989 |
| GB | 2094590 | 9/1982 |
| GB | 2164856 A | 4/1986 |
| JP | 61-94639 | 5/1961 |
| JP | 62-000327 | 1/1987 |
| JP | 3 267054 | 11/1991 |
| JP | 3267054 | 11/1991 |
| JP | 63-240851 | 10/1998 |
| WO | WO88/09151 | 12/1988 |
| WO | WO90/05494 | 5/1990 |
| WO | WO91/07726 | 5/1991 |

OTHER PUBLICATIONS

A Computer–Assisted Device for the Intraoperative CT–Correlated Localization of Brain Tumors (1988) by H. Reinhardt et al.

Friets et al., "A Framless Stereotaxic Operating Microscope for Neurosurgey", IEEE Transactions on Biomedical Engineering 36, No. 6 (Jun. 1989), pp. 608, 613–617.

"SACDAC User's Guide, Version 2e" (Mar. 1989) by PixSys, Inc., pp. 0–1 Thru 5–3.

"Offset Probe for Science Accessories' Gp–8–3d digitizer" (Dec. 1987) by PixSys, Inc., one page.

"PixSys: 3–D Digitizing Accessories" (Aug. 1989) by PixSys, Inc., 6 unnumbered pages.

"Design Aide" (Mar. 1989) by PixSys, Inc., 5 unnumbered pages.

"3–D Digitizer Captures the World" (Oct. 1990) BYTE Magazine, p. 43.

Three–Dimensional Digitizer (Neuronavigator): New Equipment for Computed Tomography–Guided Stereotaxic Surgery (1987) by Eiju Watanabe, M.D. et al.

Lecture Notes in Computer Science "Information Processing in Medical Imaging" 12th International Conference, IPMI'91, Wye UK, (Jul., 1991) front and back cover sheet only.

Brown, "A Stereotactic Head Frame for Use with CT Body Scanners," *Investigative Radiology*, 14:300–304 (Jul.–Aug. 1979).

Comeau, et al. "Headlight Television System Provides Remote Surveillance," *Research Division, Philco Corp.*, Undated.

Cosman, et al. "An Operating Arm System for Frameless Neurosurgical Procedures," Undated.

Hardy, et al. "CASS: A program for computer assisted stereotaxic surgery" (1981).

Guthrie, "Graphic–Interactive Cranial Surgery: The Operation Arm System," *Handbook of Stereotaxy Using the CRW Apparatus*, 193–210, Undated.

Kall, "The Impact of Computer and Imaging Technology on Stereotactic Surgery," *Applied Neurophysiology*, 9–22, (1987).

Kelly, "Computer Assisted Stereotactic Biopsy and Volumeric Resection of Pediatric Brain Tumors," *Brain Tumors in Children*, 9:317–336 (May, 1991).

Kelly, "Computer Directed Stereotactic Resection of Brain Tumors," *Neurological Operative Atlas*, 1:299–313, (1991).

Kelly, "Image–Directed Tumor Resection," *Neurosurgery Clinics of North America*, 1:81–95 (1990).

Kelly, "Results of Computed Tomography–based Computer–assisted Stereotactic Resection of Metastatic Intracranial Tumors," *Neurosurgery*, 22:7–17 (1988).

Kelly, "Stereotactic Craniotomy," *Stereotactic Neurosurgery*, 1:781–799 (1990).

Kelly, "Stereotactic Imaging, Surgical Planning and Computer–Assisted Resection of Intracranial Lesions: Methods and Results," Offprint from *Advances and Technical Standards in Neurosurgery*, 17:77–118 (1990).

Kim, et al. "A helmet mounted display for telerobotics," *IEEE*, 543–547 (1988).

Kwoh, et al. "A new computerized Tomographic–Aided Robotic Stereotaxis Systems," *Robotocis Age*, 2–7 (1993).

McGirr, et al. "Stereotactic Resection of Juvenile Pilocytic Astrocytomas of the Thalamus and Basal Ganglia," *Neurosurgery*, 20:447–452 (1987).

Ng, et al. "Robotic Surgery," *IEEE*, 120–125 (1993).

Tan, et al. "A frameless stereotactic approach to neurosurgical planning based on retrospective patient–image registration," *J. Neruosurg.* 79:296–303 (1993).

Thompson, et al. "A system for Anatomical and Functional Mapping of the Human Thalamus," *Computers and Biomedical Research*, 10:9–24 (1977).

Watanabe, et al. "Open Surgery Assisted by the Neuronavigator, a Stereotactic, Articulated, Sensitive Arm," *Neurosurgery*, 28:792–799 (1991).

Watanabe, et al. "Three–Dimensional Digitizer (Neuronavigator): New Equipment for Computed Tomography–Guided Stereotaxic Surgery," *Surg. Neurol.* 27:543 (1987).

Von Hanwehr, "Minimally Invasive Image–Guided Neurosurgery,," *Computerized Medical Imaging and Graphics*, 18:225–300 (1994).

Product Brochure, "Operating Arm System," Radiotronics , Inc. Product (1993).

Product Brochure, "The Viewing Wand," ISG Technologies, Inc. Product (1991).

International Search Report dated Dec. 6, 2000.

C. Pelizzari, K. Tan, D. Levin, G. Chen, J. Balter, "Interactive 3D Patient –Image Registration", Proc. $13^{th}$ Int. Conf. On Information Processing in Medical Imaging, Berlin, Germany, pp. 132–141 (1993).

PixSys, Inc., "Alignment Procedure for the PixSys Two–Emitter Offset Probe for the SAC GP–8–3d Sonic Digitizer", 3 unnumbered pages (prior to effective filing date).

* cited by examiner

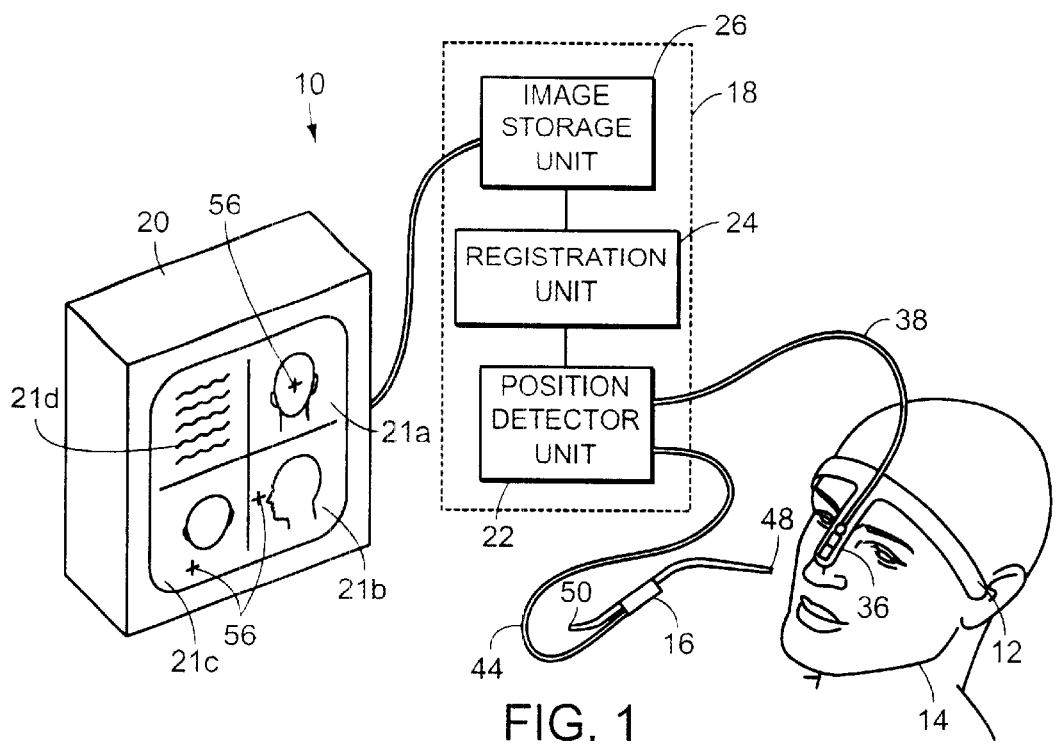
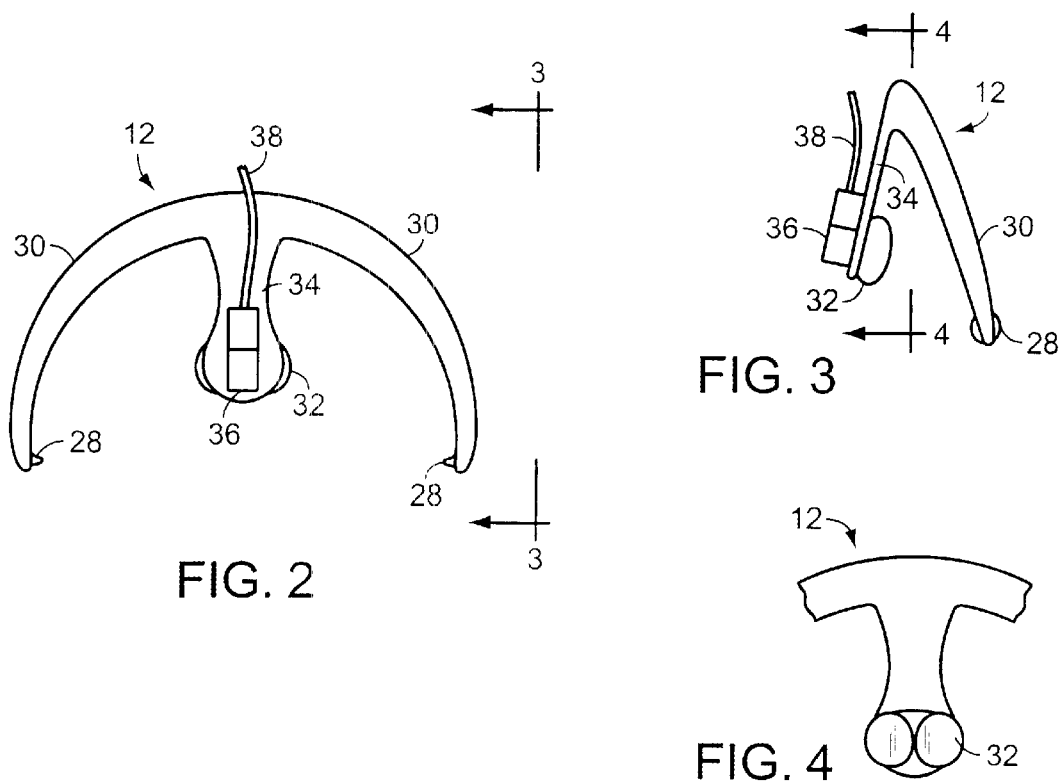

POSITION TRACKING AND IMAGING SYSTEM FOR USE IN MEDICAL APPLICATIONS

This application is a continuation of Ser. No. 08/768,305 filed Dec. 17, 1996 which is a continuation of Ser. No. 08/306,818 filed Sep. 15, 1994 now U.S. Pat. No. 5,829,444.

BACKGROUND OF THE INVENTION

The invention relates to computer assisted medical surgery and in particular relates to systems for displaying prerecorded visual images during surgical operations.

Presently available medical imaging techniques such as CAT (Computerized Axial Tomography), MRI (Magnetic Resonance Imaging), and PET (Position Emission Tomography), are known to be helpful not only for diagnostic purposes, but also for providing assistance during surgery. Prerecorded images may be displayed during surgical operations to provide the surgeon with illustrative reference mappings of pertinent portions of a patient's body.

Tracking systems for monitoring the position of a medical instrument have also been developed for use with image display systems. Generally, as the surgeon moves the medical instrument with respect to the patient's body, associated prerecorded images are displayed responsive to the movement of the instrument. Such tracking systems typically involve either the use of a passive articulated arm attached to the medical instrument, optical detection or ultrasonic detection.

Tracking systems using a passive articulated mechanical arm attached to a medical instrument are disclosed in U.S. Pat. Nos. 5,186,174 and 5,230,623. Generally, as the surgeon moves the surgical instrument with respect to the patient's body, micro recorders at the joints of the articulated arm record the respective amounts of movement of each arm member. The outputs of the micro recorders are processed and the position of the medical instrument with respect to the base of the articulated arm is thereby monitored. One or more prerecorded images are then displayed responsive to the movement of the surgical instrument. Such articulated arm tracking systems, however, require that the instrument be attached to a cumbersome mechanical arm. Also, although free movement of the tip of the arm in three dimensional space may be theoretically possible, the surgeon might experience difficulty positioning the instrument at certain locations and in desired orientations within the body.

Tracking systems using optical detection (video cameras and/or CCDs (Charge Coupled Devices)) have been proposed for monitoring the position of a medical instrument with respect to a reference unit as mentioned in U.S. Pat. No. 5,230,623. Such systems, however, require that the reference unit and the instrument both be within the view of the camera. This not only limits the movement of the surgical staff, but also requires that at least a portion of the medical instrument remain outside the patient's body.

Tracking systems using ultrasonic detection are generally disclosed in U.S. Pat. No. 5,230,623. Such systems, however, are disclosed to be used in a fashion similar to optical detection, i.e., triangulation of transmitted signals. The transmitted signals are sent from one or more senders to associated receiver(s), and the distances travelled by the signals are determined from either timing or amplitude changes. Again, the transmission path must remain unobstructed.

A further shortcoming common to each of the above tracking systems is that the patient must not move during the operation. Although the patient is likely to be generally anesthetized, the patient's body may be inadvertently moved by the surgical staff, or the surgeon may want to move the body for better positioning. If the body is moved after the tracking system has been initialized, then the tracking will be misaligned.

There is a need therefore for a system for monitoring the position of a medical instrument with respect to a patient's body that avoids the shortcomings of present devices. Specifically, there is a need for a tracking system that permits a medical instrument to be structurally unattached to a reference unit, yet capable of fully entering into the body without loss of position monitoring.

There is also a need for a tracking system that monitors the position of the patient during surgical operations.

There is also a need for a tracking system that includes a reference unit that may be easily removed from and accurately repositioned on a patient in precisely the same position. There is further a need for a position monitoring device that does not obstruct the operating space of the surgeon.

SUMMARY OF THE INVENTION

The invention relates to a system for monitoring the position of a medical instrument with respect to a patient's body and for displaying at least one of a plurality of prerecorded images of the body responsive to the position of the medical instrument. The system includes a reference unit, a remote unit, a position characteristic field generator, a field sensor, a position detection unit and an output display.

In one embodiment, the reference unit is secured from movement with respect to at least a portion of the patient's body such that the reference unit is substantially immobile with respect to a target operation site. The remote unit is attached to the medical instrument. The field generator is associated with one of the reference or remote units and generates a position characteristic field, such as a multiplexed magnetic field, in an area including the target operation site. The field sensor is associated with the other of the reference or remote units and is responsive to the presence of the field for producing a sensor output signal representative of the sensed field.

The position detection unit is in communication with the sensor output signal and produces position data representative of the position of the remote unit with respect to the reference unit. The output display unit is in communication with the position detection unit for displaying at least one of the prerecorded images responsive to the position data.

The system further may include a registration unit in communication with a storage unit and the position data. The storage unit stores the plurality of prerecorded images of the body. Each prerecorded image is representative of a planar region within the body such that the plurality of planar regions represented by the prerecorded images define a first coordinate system. The registration unit correlates the position data of a second coordinate system (as defined by the position detection unit) with the plurality of prerecorded images of the first coordinate system, and identifies a desired prerecorded image associated with the position of the remote unit with respect to the patient's body.

The invention also relates to a reference unit that is attachable to a patient's head, and a medical instrument, such as an aspirating device, that is adapted to removably receive a position detection unit.

BRIEF DESCRIPTION OF THE DRAWINGS

The following detailed description of the invention may be further understood with reference to the accompanying drawings in which:

FIG. 1 is a diagrammatic view of a system of an embodiment of the invention;

FIG. 2 is a front view of the headset unit shown in FIG. 1;

FIG. 3 is a side view of the headset unit shown in FIG. 1 taken along line 3—3 of FIG. 2;

FIG. 4 is a rear view of a portion of the headset shown in FIG. 1 taken along line 4—4 of FIG. 3;

DETAILED DESCRIPTION OF THE ILLUSTRATED EMBODIMENTS

Figures 5, 6:
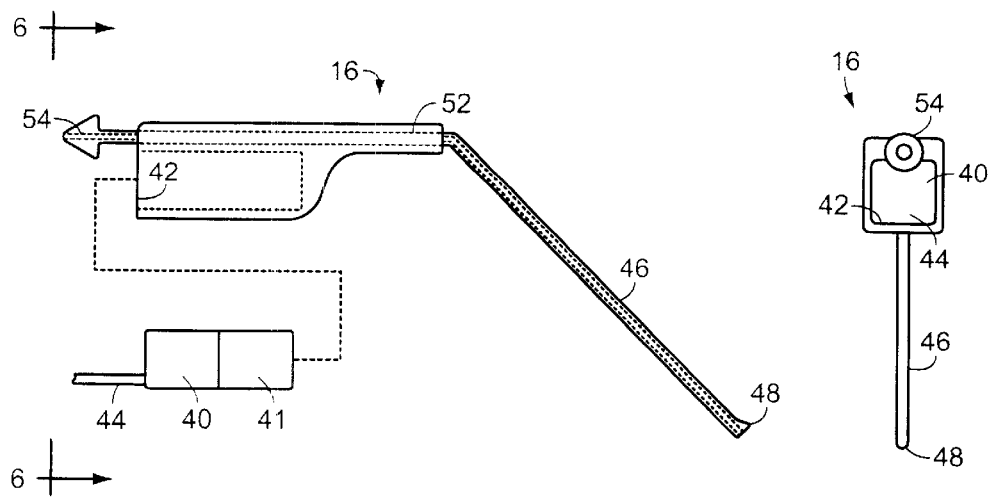
FIG. 5 is an exploded side view of the surgical instrument and remote sensor shown in FIG. 1.
FIG. 6 is an end view of the assembled surgical instrument and sensor shown in FIG. 1 taken along line 6—6 of FIG. 5.

As shown in FIG. 1, a system 10 of the invention includes a headset 12 mounted on a patient 14, a medical instrument 16, a control system 18 and a display 20. The control system 18 includes a position detection unit 22, a registration unit 24, and an image storage unit 26.

The image storage unit 26 stores sets of prerecorded images such as CAT, MRI or PET scan images. Each set of images may be taken along, for example, coronal, sagittal or axial directions. As shown in FIG. 1, the display 20 shows three images, a coronal image 21a, a sagittal image 21b, and an axial image 21c. Text information may also be displayed as shown at 21d in FIG. 1.

As further shown in FIGS. 2–4, the headset 12 includes two ear mounts 28 on side members 30, and a nose bridge mount 32 on a center member 34. The headset 12 should be made of a resilient plastic such that it may be snugly attached to a patient's head, and may be provided in a variety of sizes. A primary objective of the headset is to provide a reference unit that may be easily attached to and removed from a patient's head wherein the headset may be repeatedly reattached in exactly the same place with a high degree of accuracy. In other embodiments, the side members 30 of the headset 12 may be rotationally attached to one another and the ear mounts 28 may be biased toward one another. Further, the center member 34 may be rotatable with respect to the side members 30 and biased toward the ear mounts 28 as well.

The headset 12 shown in FIGS. 1–4 also includes a reference unit 36 connected to the position detection unit 22 via communication lines 38. The reference unit 36 may be releasably attached to the headset 12 by conventional clamp or fastening means. In one embodiment the reference unit 36 may include a position characteristic field generator capable of generating a multidirectional field in three dimensions and may involve the use of either electromagnetic or ultrasonic waves. The position characteristic field differs from the transmit/receive triangulation system, in part, because it does not rely on the comparison of one transmitted signal with another as does triangulation. This permits the path between the field generator and the remote sensor to be obstructed by materials that do not significantly alter the generated field. For example, the position of the medical instrument could be identified even when the instrument is within the patient's body when the generated field in a magnetic field. Additionally, the reference unit may also include a reference sensor 37 to provide verification of proper system operation.

In the present embodiment the field generator includes three orthogonally disposed magnetic dipoles (e.g., current loops or electromagnets), and the orthogonally disposed magnetic fields generated by each of the three dipoles are mutually distinguishable from one another (e.g., via either phase, frequency, or time division multiplexing). The near-field characteristics of the multiplexed magnetic fields may be relied upon for position detection, for example as generally described in U.S. Pat. No. 4,054,881. Since the presence of magnetic material might interfere with the magnetic fields these materials are to be avoided in such an electromagnetic system. In alternate embodiments the field generator may be located somewhere other than on the headset and the headset may include two field sensors 36,37. When the distance between the sensors 36,37 is known, the second sensor acts as a backup or reference check for monitoring the proper operation of the system. If the sensed fields are inconsistent then an error signal is displayed and/or sounded.

In other embodiments the headset 12 may be employed in systems based on the triangulation of signals where the reference unit 36 includes one or more signal transmitters and/or one or more signal receivers. In such a triangulation system, position detection is achieved by comparing certain characteristics of one transmitted signal with those of a second transmitted signal to determine the relative distances travelled. The transmitted signals may be electromagnetic (e.g., radio, laser light or light emitting diodes) or may be ultrasonic. The position of the patient's head with respect to the surgical instrument may thereby be monitored.

As shown in FIGS. 5 and 6 the medical instrument 16 may be an aspirating device adapted to removably receive a remote sensor 40 for detecting, for example, the field generated by the position characteristic field generator. The sensor 40 may be held inside the instrument 16 by force fit sizing or through the use of a resilient snap member in the wall opening 42. Since an aspirating device is commonly used in most surgical operations, incorporating the remote sensor into the aspirating device provides the surgeon with a convenient position detection device that does not clutter the operation site with unnecessary items. The instrument 16 may further include a second backup field sensor 41 for system error detection as discussed above with reference to the sensor 37.

The remote sensors 40,41 are removable from the aspirating device and may be interchangeably inserted into any of a variety of specially adapted surgical instruments. In the illustrated embodiment, the remote sensors 40,41 are received through an opening 42 in the proximal end of the instrument 16, and are connected to the position detection unit 22 via communication lines 44. The sensors 40,41 may also each include three orthogonally disposed dipole sensing elements for detecting the presence of the field generated by the field generator. For example, in one embodiment, the field generator and the sensors each include three orthogonally disposed electrical wire loops. The generator produces an alternating current through one generator loop at a time thus generating a time division multiplexed alternating electromagnetic field. The sensor loop signals are each processed in synchronous timing with the generator loops to produce outputs responsive to each respective alternating electromagnetic field.

The distal end of the instrument 16 includes a rigid aspirating tube 46 having a flared tip 48. The position of the tip 48 with respect to the center of the remote sensor 40 is a known constant and may be easily seen by the surgeon during surgery. The aspirating tube 46 is in fluid communication with an aspirating catheter 50 through the proximal end of the instrument 16 via internal channel 52 and a connector element 54. The aspirating catheter 50 (shown in FIG. 1) is connected to a vacuum aspirating unit (not shown).

In operation, the position detection unit monitors the position of the medical instrument 16 with respect to the reference unit 36. The registration unit 24 correlates the changes in position of the instrument 16 with the spacial orientation of the stored images. As the surgeon moves the medical instrument 16, images appear on the display 20 responsive to the position of the medical instrument 16. This permits the surgeon to always have available the coronal, sagittal, and axial views associated with the precise location of the tip 48 of the instrument 16 regardless of whether the tip 48 is inside of the patient 14. Moreover, since the field generator is attached to the patient's head, the patient is free to be moved without loss of the tracking capabilities. The display 20 may further identify the location of the tip 48 on each of the displayed images as shown at 56 in FIG. 1. In other embodiments the orientation of the aspirating tube 46 may also be identified on the displayed images. In further embodiments, a three dimensional composite image may be displayed based on the prerecorded images.

Figure 7:
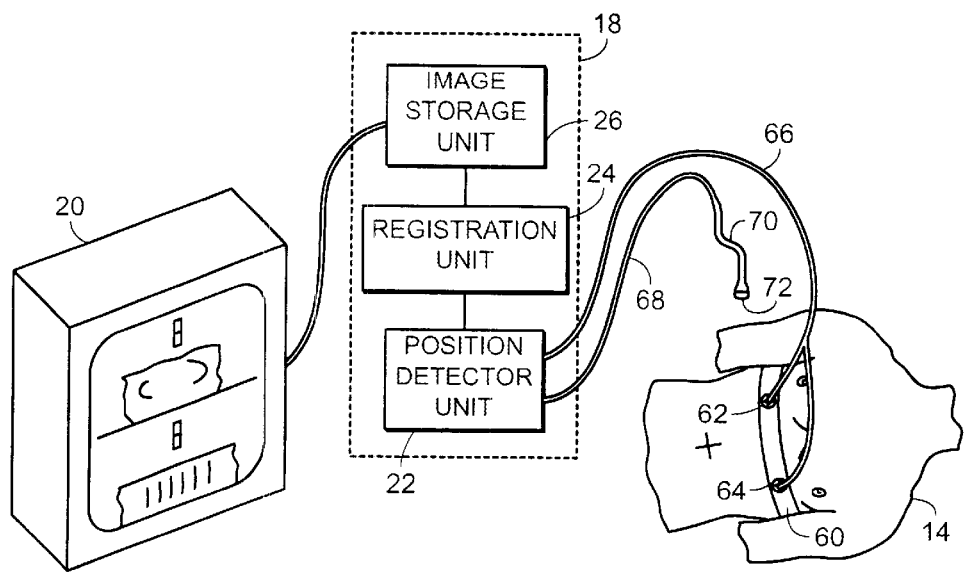
FIG. 7 is a diagrammatic view of an alternate embodiment of the invention.

As shown in FIG. 7 in an alternate embodiment, the system may include a flexible band 60 for secure attachment to a portion of a patient's body 14 (e.g., a head or chest). The band 60 includes field generator 62 and a reference sensor 64 that provides feedback to the signal generator in the position detection unit 22. The position detection unit 22 is connected via communication lines 66 to the flexible band 60, and is connected via communication lines 68 to a flexible medical instrument 70 having a remote sensor at its tip 72. Because the medical instrument 70 is not rigid, the sensor should be positioned sufficiently close to the tip of the instrument 70 to provide accurate position detection and monitoring within the patient's body. The display 20 may indicate the relative orientation of the instrument 70 on one or more images as shown.

Figure 8:
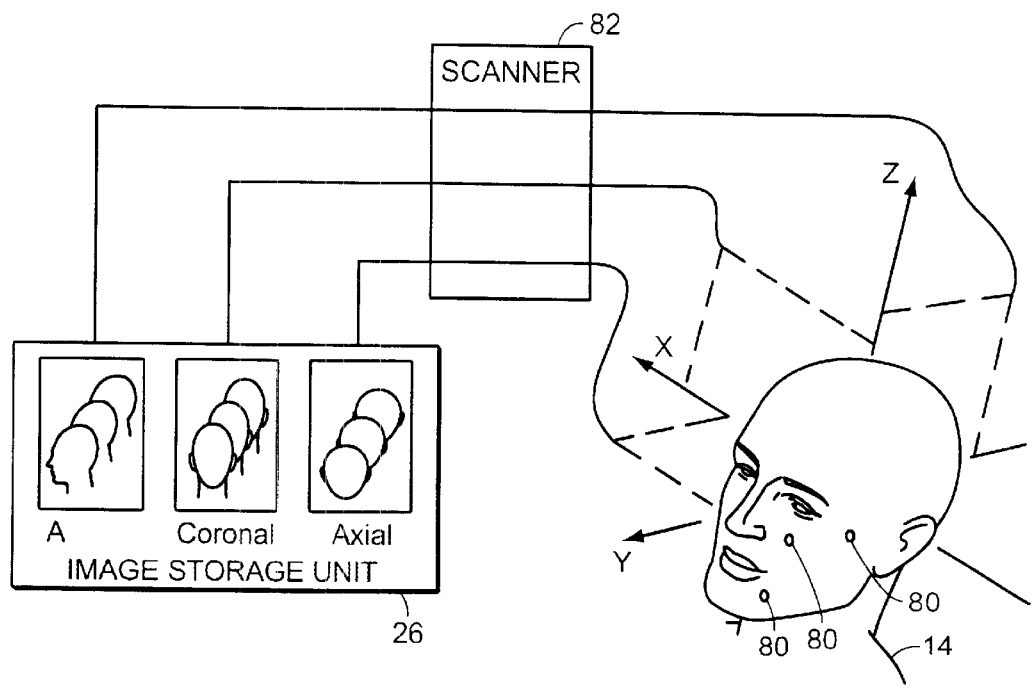
FIGS. 8 and 9 are diagrammatic views of image recording and registration operations of the invention.
Figure 9:
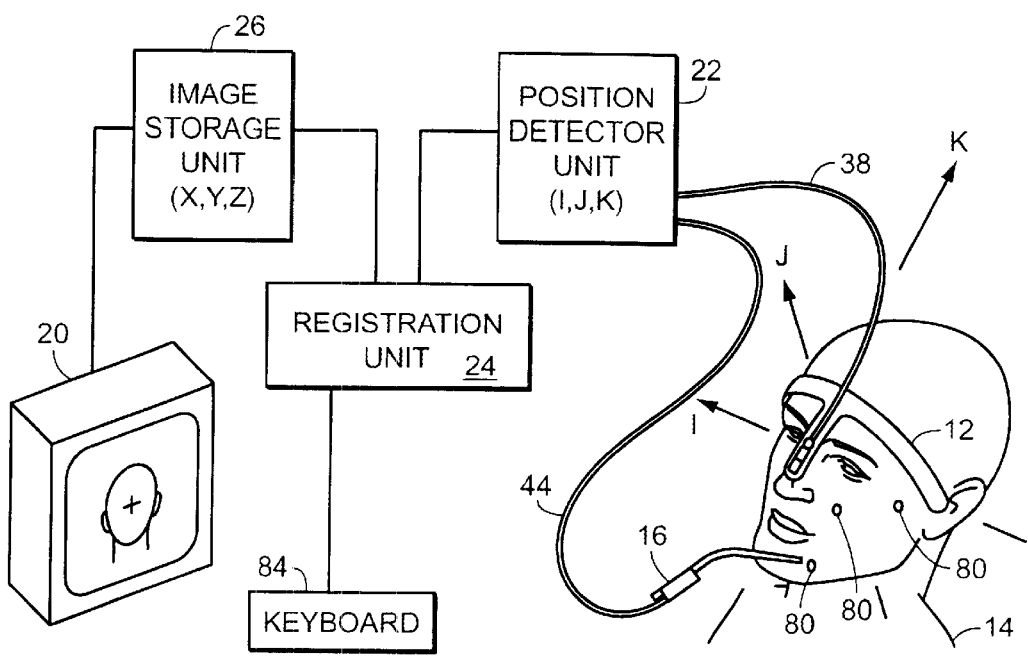

As illustrated in FIGS. 8 and 9 the registration process involves two fundamental steps: 1) recording the scan images of a predetermined orientation and 2) mapping the spacial orientation of the position detection system onto the recorded images. For example, the orientations of the prerecorded images may be in the sagittal (y-z plane), coronal (x-z plane) and/or axial (x-y plane) as shown in FIG. 8. The images may be digitally stored and the distance between each scanned image is recorded, as are the relative orientations of each set of images.

In one embodiment, fiducial markers 80 are placed on the patient's head 14 prior to scanning with the scanner 82. The markers then appear on certain of the scanned images, and may be located by the position detection system as shown in FIG. 9. Specifically, when each marker 80 is sequentially located, for example with the tip 48 of a medical instrument 16, the user signals the registration unit, such as via a computer keyboard 84.

The registration unit then scans each recorded digital image beginning from one corner until it locates the identified marker. In other embodiments this may be achieved by having the images appear on the display 20 and having the user identify the markers by using a keyboard or mouse. Once each of the markers have been located using the position detection unit, the registration unit generates a mapping function to translate the position detection data (in i-j-k coordinates) to the stored image orientation data (in x-y-z coordinates).

In other embodiments, the patient may be wearing an attached reference unit, such as the headset 12, when the scan images are recorded. Based on the predefined structure of the reference unit, the registration unit may then automatically locate portions of the reference unit on the scanned images, thereby identifying the orientation of the reference unit with respect to the scanned images. Since the relative orientation of the field generator with respect to the reference unit is known, the registration unit may then generate the appropriate mapping function. In further embodiments the surfaces of the patient's skin may be tracked such as by a laser light pointer or a movable tip pointer that is biased in a forward direction. The tracked surfaces may then be located on the stored images. In still further embodiments, the registration unit could be programmed to identify characteristic structures or features of the patient's body and thereby provide fully automatic registration. For example, the system might, knowing the size and shape of a headset, identify where the headset would be placed on the patient's head, even though it does not appear on the prerecorded images.

As discussed above the position detection system may operate by any desired principles suitable for generating a field in which position detection may be achieved at any location within the field. For example, applicants have found that the 3 Space® Fastrak™ product sold by Polhemus, Incorporated of Colchester, Vermont operates via principles suitable for use in the present invention. This product uses three orthogonally disposed coil loops for both the transmitter and the sensors, and produces alternating electromagnetic fields of 8–14 khz that are time division multiplexed. Those skilled in the art will appreciate that the relative positioning of the field generator and the one or more field sensors is in no way limited to those shown in FIGS. 1 and 7.

Figure 10:
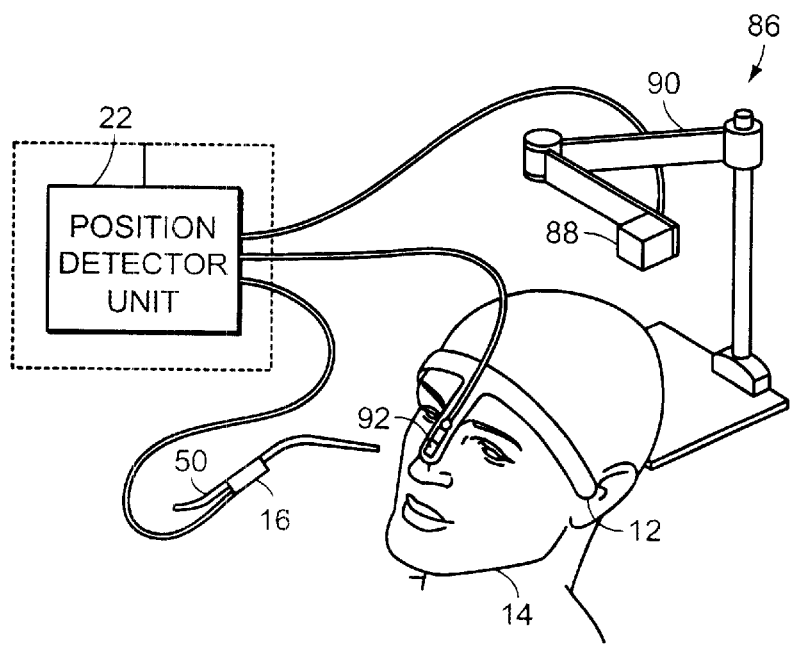
FIGS. 10–13 are diagrammatic views of further embodiments of the invention.

As shown in FIG. 10, in alternate embodiments of the invention a reference unit 86, including a field generator 88, may be positioned a small distance away from the portion of the patient's body (such as the head) 14 on an articulated arm 90. A headset 12 including a reference sensor 92 may be attached to the patient's body, and the medical instrument 16 may include a remote sensor 40 as discussed above with reference to FIGS. 1–6. Once the field generator 88 is positioned at a convenient location it may be fixed in place by securing the joints of the articulated arm. The position of the patient with respect to the field generator may accordingly be monitored. The position of the instrument 16 with respect to the patient may also be determined and the system may then operate to display the appropriate prerecorded images as discussed above.

In other embodiments, the position of the field generator 88 may be adjusted during the surgical operation by moving the articulated joints. If neither the remote sensor 40 nor the reference sensor 92 are moved with respect to one another, then moving the field generator 88 should not affect the position detection system. If the accuracy of the system depends at all on the relative positions of the field generators 88 and the sensors 40, 92, then it may be desirable to move the field generator 88 during the surgical operation. This may be the case, for example, if the system relies on the near-field characteristics of a multiplexed magnetic field wherein it might be desirable to keep the sensors 40, 92 generally equidistant from the generator 88. In still further embodiments, the system may periodically prompt the user to reposition the generator 88 such as through visual cues on the display.

Figure 11:
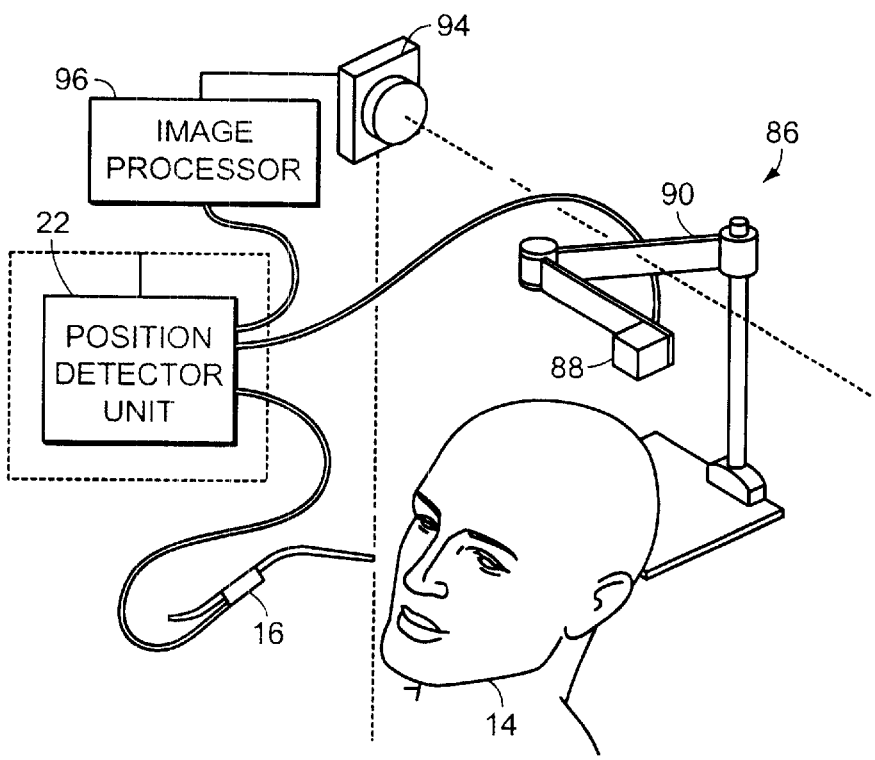

The monitoring of the position of the patient may be accomplished by means other than using a headset and reference sensor. For example, a camera 94 connected to an image processor 96 may be positioned to record the location of the field generator with respect to the target operation site of the patient as shown in FIG. 11. If either the patient or the field generator is moved, the image processor 96 will identify the amount of relative change in location and advise the position detection unit 22 accordingly. Additional cameras positioned to view the patient from a variety of directions may be employed in further embodiments.

Figure 12:
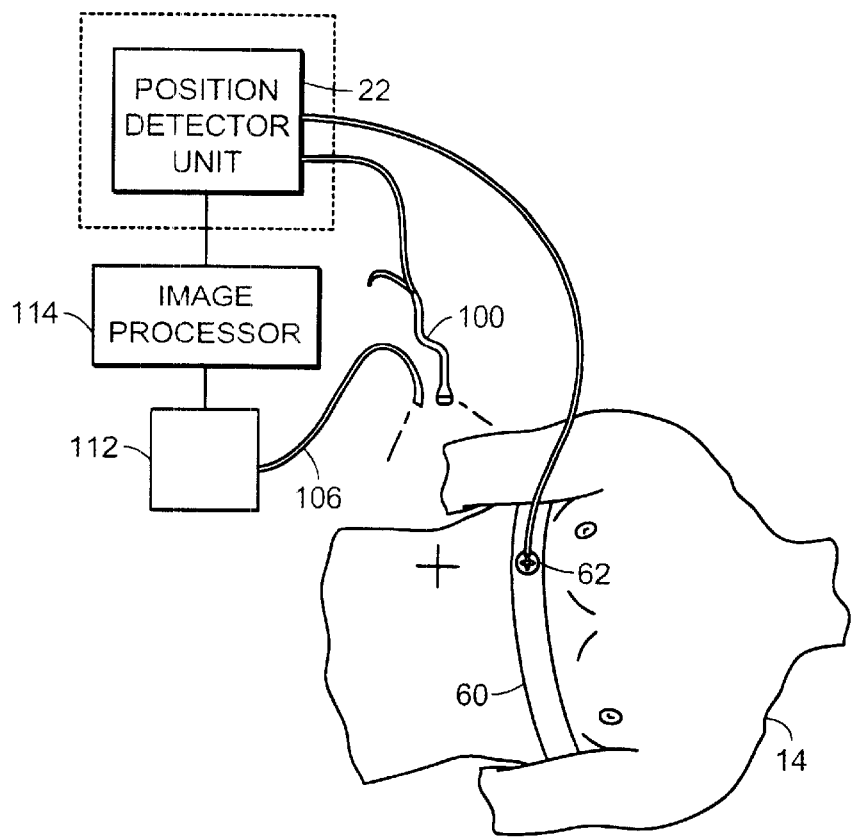
Figure 13:
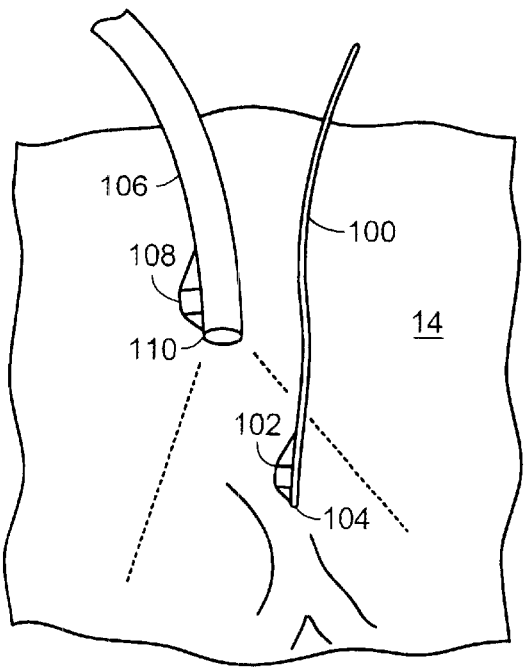

As shown in FIGS. 12 and 13 a system of the invention may include a flexible medical instrument 100 having a sensor 102 at its distal tip 104, and a fiber optic endoscope 106 having a sensor 108 at it distal tip 110. The fiber optic endoscope 106 is connected at its proximal end to a camera 112 which is in communication with an image processor 114. Because the field generator 62 on the reference band 60 may move, for example as the patient breaths, the location of the remote sensor 102 may appear to move when in fact the medical instrument 100 has not moved.

To correct for this problem, the fiber optic endoscope 106 can be used to monitor the position of the tip 104 of the instrument 100 with respect to the inside of the patient's body as shown. Any sensed movement of the sensor 102 with respect to the field generator 62 can be evaluated with reference to whether the tip 104 has moved with respect to the interior of the patient's body. If the camera observes that the tip 104 has not moved, but the sensor 102 indicates that it has moved, then the system can identify that such movement was due to the movement of the field generator and not the sensor 102. The system may then automatically correct for such variation. Further, the fiber optic endoscope 106 itself may include a sensor 108 for detecting whether the tip 110 of the fiber optic has moved. This should further enhance the accuracy of the correction system. Also, the camera 112 may provide continuous registration of the prerecorded images based on the internal structure of the patient's body.

It will be understood by those skilled in the art that numerous variations and modifications may be made to the above described embodiments without departing from the spirit and scope of the present invention.

We claim:

1. A system for monitoring a position of a medical instrument with respect to a patient's body and for displaying images of the patient's body responsive to the position of the medical instrument, said system comprising:
    input means for communicating with image data, said image data representing a plurality of images of the patient's body;
    a patient reference unit securable from movement with respect to the patient's body yet permitting the patient's body to be moved within an operating environment;
    a remote unit securable from movement with respect to the medical instrument;
    an operating environment reference unit capable of being positioned within an operating environment;
    at least one field generator means associated with at least one of said patient reference unit, said remote unit, or said operating environment reference unit, said field generator means for generating a position characteristic field capable of passing through the patient's body and being substantially undisturbed by passage through the patient's body;
    at least one field sensor means associated with another of said patient reference unit, said remote unit, and said operating environment reference unit, said field sensor means for producing a sensor output signal responsive to the presence of said position characteristic field, said sensor output signal being representative of a position of said sensor relative to said field generator irrespective of whether any portion of the patient's body is interposed between said field generator means and said field sensor means;
    position detection means in communication with said field generator means and said field sensor means, said position detection means for producing position data responsive to said sensor output signal representative of a position of said remote unit with respect to said reference unit irrespective of any movement of the patient within the operating environment;
    tracking means in communication with said input means and said position detection means, said tracking means for selecting from said image data position image data associated with said position data; and
    output display means in communication with said tracking means for displaying an image of the patient's body responsive to said position image data, said position image data varying for different position data.

2. A system as claimed in claim 1, wherein said field generator means includes an electromagnetic field generator that is attached to said patient reference unit, and said field sensor means includes an electromagnetic field sensor that is attached to said remote unit.

3. A system as claimed in claim 1, wherein said field generator means includes an electromagnetic field generator that is attached to said operating environment reference unit, and said field sensor means includes an electromagnetic field sensor that is attached to said remote unit.

4. A system as claimed in claim 1, wherein said system includes a reference sensor positioned a fixed distance from either of said field generator means or said field sensor means, said reference sensor for producing a reference output signal for use in monitoring the field generated by said field generator means.

5. A system as claimed in claim 1, wherein said position characteristic field comprises a non-linear field that emanates from substantially a singular point.

6. A system as claimed in claim 1, wherein said position characteristic field comprises at least two time multiplexed fields that emanate from substantially the same point.

7. A system as claimed in claim 1, wherein said position characteristic field comprises at least three time multiplexed fields that emanate from substantially the same point.

8. A system as claimed in claim 1, wherein said patient reference unit includes a headset comprising two ear mounting elements for engaging ear canal openings of the patient's body, and a nose mounting element for engaging a nose bridge of the patient's body.

9. A system as claimed in claim 8, wherein each said mounting element is disposed on a distal end of an elongated mounting arm.

10. A system as claimed in claim 8, wherein said patient reference unit comprises a structurally resilient material.

11. A system as claimed in claim 8, wherein said patient reference unit includes a flexible band for attachment to a portion of the patient's body.

12. A system as claimed in claim 11, wherein said flexible band further includes at least one reference sensor for producing a reference sensor output signal representative of a position of said reference sensor relative to said field generator.

13. A system as claimed in claim 1, wherein said medical instrument includes a flexible member for insertion into the patient's body, and said remote unit includes a field sensor at a distal end of said flexible member.

14. A system as claimed in claim 1, wherein said images include prerecorded scan images, and said system further includes registration means for registering a spatial orientation of said prerecorded scan images with a spatial orientation of said position characteristic field.

15. A system as claimed in claim 1, wherein said output display means includes means for displaying on said images an indicator representative of a location of said medical instrument with respect to the patient's body responsive to said position data.

16. A system as claimed in claim 1, wherein said operating environment reference unit comprises a support unit for supporting at least a portion of the patient's body.

17. A system as claimed in claim 1, wherein said operating environment reference unit comprises an articulated arm.

18. A system for monitoring a position of a medical instrument with respect to a patient's body and for displaying images of the patient's body responsive to the position of the medical instrument, said system comprising:

input means for communicating with image data, said image data representing a plurality of images of the patient's body;

a patient reference unit securable from movement with respect to the patient's body yet permitting the patient's body to be moved within an operating environment;

a remote unit securable from movement with respect to the medical instrument;

an operating environment reference unit capable of being positioned within an operating environment;

at least one field generator means associated with at least one of said patient reference unit, said remote unit, or said operating environment reference unit, said field generator means for generating a position characteristic field capable of passing through the patient's body and being substantially undisturbed by passage through the patient's body;

at least one field sensor means associated with at least one of said patient reference unit, said remote unit, and said operating environment reference unit, said field sensor means for producing a sensor output signal responsive to the presence of said position characteristic field, said sensor output signal being representative of a position of said sensor relative to said field generator irrespective of whether any portion of the patient's body is interposed between said field generator means and said field sensor means;

position detection means in communication with said field generator means and said field sensor means, said position detection means for producing position data responsive to said sensor output signal representative of a position of said remote unit with respect to said reference unit irrespective of any movement of the patient within the operating environment;

tracking means in communication with said input means and said position detection means, said tracking means for selecting from said image data position image data associated with said position data; and output display means in communication with said tracking means for displaying an image of the patient's body responsive to said position image data, said position image data varying for different position data.

19. A system as claimed in claim 18, wherein said operating environment reference unit comprises a support unit for supporting at least a portion of the patient's body.

20. A system as claimed in claim 18, wherein said operating environment reference unit comprises an articulated arm.

21. A system as claimed in claim 18, wherein said position characteristic field comprises a non-linear field that emanates from a substantially point source.

22. A system as claimed in claim 18, wherein said position characteristic field comprises a non-linear field that emanates from one side only of said patient.

23. A system as claimed in claim 18, wherein said system includes a reference sensor positioned a fixed distance from either of said field generator means or said field sensor means, said reference sensor for producing a reference output signal for use in monitoring the field generated by said field generator means.

24. A system for monitoring a position of a medical instrument with respect to a patient's body and for displaying images of the patient's body responsive to the position of the medical instrument, said system comprising:

image data means for communicating with image data, said image data representing a plurality of images of the patient's body;

a patient reference unit securable from movement with respect to the patient's body yet permitting the patient's body to be moved within an operating environment;

a remote unit securable from movement with respect to the medical instrument;

an operating environment reference unit capable of being positioned within an operating environment;

at least one field generator means associated with at least one of said patient reference unit, said remote unit, or said operating environment reference unit, said field generator means for generating an electromagnetic position characteristic field capable of passing through the patient's body and being substantially undisturbed by passage through the patient's body;

at least one field sensor means associated with at least one of said patient reference unit, said remote unit, and said operating environment reference unit, said field sensor means for producing a sensor output signal responsive to the presence of said position characteristic field, said sensor output signal being representative of a position of said sensor relative to said field generator irrespective of whether any portion of the patient's body is interposed between said field generator means and said field sensor means;

position detection means in communication with said field generator means and said field sensor means, said position detection means for producing position data responsive to said sensor output signal representative of a position of said remote unit with respect to said reference unit irrespective of any movement of the patient within the operating environment; and tracking means in communication with said image means and said position detection means, said tracking means for selecting from said image data position image data associated with said position data.

25. A system as claimed in claim 24, wherein said system includes a reference sensor positioned a fixed distance from either of said field generator means or said field sensor means, said reference sensor for producing a reference output signal for use in monitoring the field generated by said field generator means.

26. A system for monitoring a position of a medical instrument with respect to a patient's body and for displaying images of the patient's body responsive to the position of the medical instrument, said system comprising:
- a patient reference unit securable from movement with respect to the patient's body yet permitting the patient's body to be moved within an operating environment;
- a remote unit securable from movement with respect to the medical instrument;
- an operating environment reference unit capable of being positioned within an operating environment;
- at least one field generator associated with at least one of said patient reference unit, said remote unit, and said operating environment reference unit, said field generator being configured to generate a position characteristic field capable of passing through the patient's body and being substantially undisturbed by passage through the patient's body;
- at least one field sensor associated with another of said patient reference unit, said remote unit, and said operating environment reference unit, said field sensor being configured to produce a sensor output signal responsive to the presence of said position characteristic field, said sensor output signal being representative of a position of said field sensor relative to said field generator irrespective of whether any portion of the patient's body is interposed between said field generator and said field sensor;
- a position detection unit in communication with said field generator and said field sensor, said position detection unit being configured to produce position data responsive to said sensor output signal representative of a position of said remote unit with respect to said patient reference unit irrespective of any movement of the patient within the operating environment;
- a registration unit in communication with said position detection unit and with image data representing a plurality of images of the patient's body, said registration unit being configured to select from said image data position image data associated with said position data; and
- an output display in communication with said registration unit, said output display being configured to display an image of the patient's body responsive to said position image data, said position image data varying for different position data.

27. A system as claimed in claim 26, wherein said field generator includes an electromagnetic field generator that is attached to said reference unit, and said field sensor includes an electromagnetic field sensor that is attached to said remote unit.

28. A system as claimed in claim 26, wherein said filed generator includes an electromagnetic filed generator that is attached to said operating environment reference unit, and said field sensor includes an electromagnetic field sensor that is attached to said remote unit.

29. A system as claimed in claim 26, wherein said system includes a reference sensor positioned a fixed distance from either of said field generator or said field sensor, said reference sensor for producing a reference output signal for use in monitoring the field generated by said field generator.

30. A system as claimed in claim 26, wherein said position characteristic field comprises a non-linear field that emanates from substantially a singular point.

31. A system as claimed in claim 26, wherein said position characteristic field comprises at least two time multiplexed fields that emanate from substantially the same point.

32. A system as claimed in claim 26, wherein said position characteristic field comprises at least three time multiplexed fields that emanate from substantially the same point.

33. A system as claimed in claim 26, wherein said patient reference unit includes a headset comprising two ear mounting elements for engaging ear canal openings of the patient's body, and a nose mounting element for engaging a nose bridge of the patient's body.

34. A system as claimed in claim 33, wherein each said mounting element is disposed on a distal end of an elongated mounting arm.

35. A system as claimed in claim 33, wherein said patient reference unit comprises a structurally resilient material.

36. A system as claimed in claim 26, wherein said patient reference unit includes a flexible band for attachment to a portion of the patient's body.

37. A system as claimed in claim 36, wherein said flexible band further includes at least one reference sensor for producing a reference sensor output signal representative of a position of said reference sensor relative to said field generator.

38. A system as claimed in claim 26, wherein said medical instrument includes a flexible member for insertion into the patient's body, and said remote unit includes a field sensor at a distal end of said flexible member.

39. A system as claimed in claim 26, wherein said images include prerecorded scan images, said registration unit being configured to register a spatial orientation of said prerecorded scan images with a spatial orientation of said position characteristic field.

40. A system as claimed in claim 26, wherein said output display is configured to display on said images an indicator representative of a location of said medical instrument with respect to the patient's body responsive to said position data.

41. A system as claimed in claim 26, wherein said operating environment reference unit comprises a support unit for supporting at least a portion of the patient's body.

42. A system as claimed in claim 26, wherein said operating environment reference unit comprises an articulated arm.

43. A system for monitoring a position of a medical instrument with respect to a patient's body and for displaying images of the patient's body responsive to the position of the medical instrument, said system comprising:
- a patient reference unit securable from movement with respect to the patient's body yet permitting the patient's body to be moved within an operating environment;
- a remote unit securable from movement with respect to the medical instrument;
- an operating environment reference unit capable of being positioned within an operating environment;
- at least one field generator associated with at least one of said patient reference unit, said remote unit, and said operating environment reference unit, said field generator being configured to generate a position characteristic field capable of passing through the patient's body and being substantially undisturbed by passage through the patient's body;
- at least one field sensor associated with at least one of said patient reference unit, said remote unit, and said operating environment reference unit, said field sensor being configured to produce a sensor output signal responsive to the presence of said position characteristic field, said sensor output signal being representative of a position of said field sensor relative to said field generator irrespective of whether any portion of the patient's body is interposed between said field generator and said field sensor;

a position detection unit in communication with said field generator and said field sensor, said position detection unit being configured to produce position data responsive to said sensor output signal representative of a position of said remote unit with respect to said patient reference unit irrespective of any movement of the patient within the operating environment;

a registration unit in communication with said position detection unit and with image data representing a plurality of images of the patient's body, said registration unit being configured to select from said image data position image data associated with said position data; and an output display in communication with said registration unit, said output display being configured to display an image of the patient's body responsive to said position image data, said position image data varying for different position data.

44. A system as claimed in claim 43, wherein said operating environment reference unit comprises a support unit for supporting at least a portion of the patient's body.

45. A system as claimed in claim 43, wherein said operating environment reference unit comprises an articulated arm.

46. A system as claimed in claim 43, wherein said position characteristic field comprises a non-linear field that emanates from a substantially point source.

47. A system as claimed in claim 43, wherein said position characteristic field comprises a non-linear field that emanates from one side only of said patient.

48. A system as claimed in claim 43, wherein said system includes a reference sensor positioned a fixed distance from either of said field generator or said field sensor, said reference sensor for producing a reference output signal for use in monitoring the field generated by said field generator.

49. A system for monitoring a position of a medical instrument with respect to a patient's body and for displaying images of the patient's body responsive to the position of the medical instrument, said system comprising:

a patient reference unit securable from movement with respect to the patient's body yet permitting the patient's body to be moved within an operating environment;

a remote unit securable from movement with respect to the medical instrument;

an operating environment reference unit capable of being positioned within an operating environment;

at least one field generator associated with at least one of said patient reference unit, said remote unit, and said operating environment reference unit, said field generator being configured to generate an electromagnetic position characteristic field capable of passing through the patient's body and being substantially undisturbed by passage through the patient's body;

at least one field sensor associated with at least one of said patient reference unit, said remote unit, and said operating environment reference unit, said field sensor being configured to produce a sensor output signal responsive to the presence of said position characteristic field, said sensor output signal being representative of a position of said field sensor relative to said field generator irrespective of whether any portion of the patient's body is interposed between said field generator and said field sensor;

a position detection unit in communication with said field generator and said field sensor, said position detection unit being configured to produce position data responsive to said sensor output signal representative of a position of said remote unit with respect to said patient reference unit irrespective of any movement of the patient within the operating environment; and a registration unit in communication with said position detection unit and with image data representing a plurality of images of the patient's body, said registration unit being configured to select from said image data position image data associated with said position data.

50. A system as claimed in claim 49, wherein said system includes a reference sensor positioned a fixed distance from either of said field generator or said field sensor, said reference sensor for producing a reference output signal for use in monitoring the field generated by said field generator.

* * * * *